United States Patent [19]

Lim

[11] Patent Number: 4,830,011

[45] Date of Patent: May 16, 1989

[54] CATHETER TIP POLAROGRAPHIC LACTIC ACID AND LACTATE SENSOR FOR EXTENDED USE IN VIVO

[76] Inventor: Shun P. Lim, 2956 Ontario La., Bismarck, N. Dak. 58501

[21] Appl. No.: 103,020

[22] Filed: Sep. 30, 1987

[51] Int. Cl.$^4$ ............................................... A61B 5/00
[52] U.S. Cl. .................................... 128/635; 204/403; 204/415
[58] Field of Search ................. 128/635; 204/403, 415

[56] References Cited

U.S. PATENT DOCUMENTS

| | | | |
|---|---|---|---|
| 3,791,376 | 2/1974 | Rybak | 204/403 X |
| 4,240,889 | 12/1980 | Yoda et al. | 204/403 |
| 4,467,811 | 8/1984 | Clark, Jr. | 128/635 |
| 4,680,268 | 7/1987 | Clark, Jr. | 128/635 X |

FOREIGN PATENT DOCUMENTS 0169668 10/1982 Japan .................................... 128/635

OTHER PUBLICATIONS

Racine et al., "An Instrument . . . L-Lactate . . . ", Med. Inst., vol. 9, No. 1, Jan.-Feb. 1975, pp. 11-14.

Primary Examiner—Lee S. Cohen
Attorney, Agent, or Firm—Frost & Jacobs

[57] ABSTRACT

A polarographic sensor capable of monitoring lactic acid and lactate levels which can be incorporated on catheters to permit the in vivo study of lactate metabolism. A catheter may be directed to various parts of the vascular system by fluoroscopy so that the lactic acid and lactate concentrations at a specific site may be monitored. The present invention makes it possible to continuously monitor lactate metabolism for an extended period of time.

24 Claims, 4 Drawing Sheets

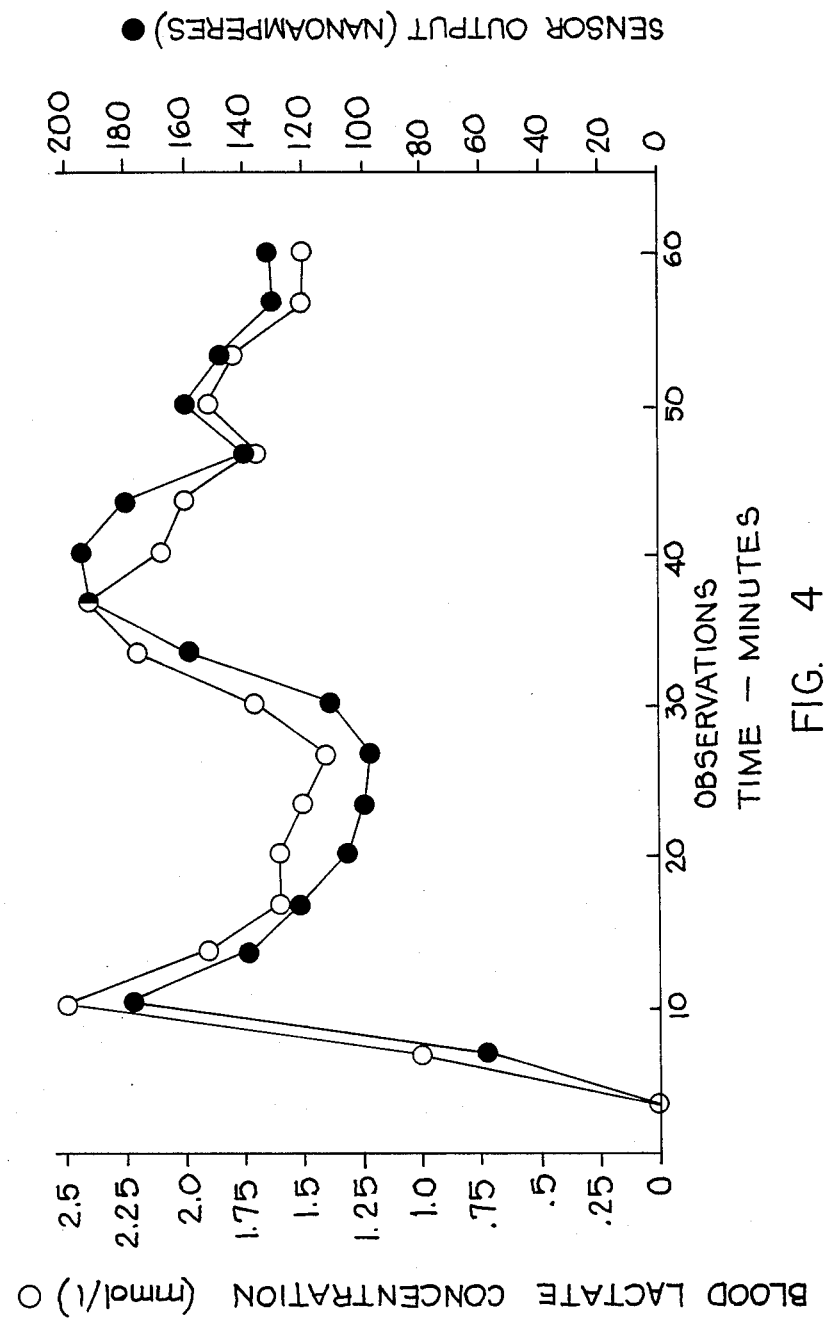

CATHETER TIP POLAROGRAPHIC LACTIC ACID AND LACTATE SENSOR FOR EXTENDED USE IN VIVO

BACKGROUND OF THE INVENTION

1. Field of the Invention

The present invention relates to a polarographic sensor for monitoring lactic acid and lactate levels in the vascular system, and in particular to a polarographic sensor incorporated on a catheter to permit the in vivo study of lactate metabolism at a specific site in a mammal body.

2. Description of the Prior Art

The role of lactate as the most reliable metabolic indicator of anaerobiosis has long been appreciated in physiology and clinical medicine. Lactate is currently regarded as the best single measurement for the immediate diagnosis, quantitation of the severity, and prognosis of shock states. It is also an indicator of prognosis in acute myocardial infarction and myocardial failure. In sports medicine and exercise physiology, blood lactate levels measure anaerobic capacity and can be used to evaluate the effectiveness of training, predict endurance and detect over-training.

For many years it has been known in the art that enzyme-coupled electrodes are useful for polarographic analysis of certain substances. For example, U.S. Pat. No. 3,539,455 discloses the membrane polarographic electrode system method for the rapid and accurate quantitative analysis of glucose levels in blood. U.S. Pat. No. 4,356,074 discloses an invention wherein the relative specificity of the enzyme galactose oxidase for various substrate materials to be determined polarographically is controlled as a function of a redox potential applied to the enzyme. U.S. Pat. No. 4,404,066 discloses an invention wherein any multisubstrate enzyme having a redox potential resulting in a direct activity dependent upon potential may be controlled wherein the relative activity of the enzyme formed in an enzyme electrode is controlled as a function of a redox potential applied to the enzyme.

In addition, recent advances have been made for analyzing lactic acid and lactate levels. In U.S. Pat. No. 4,005,002 and U.S. Pat. No. 4,129,478, Racine et al. disclose a method based on the highly specific oxidation of lactate to pyruvate in the presence of the enzyme cytochrome $b_2$ and hexacyanoferrate-(III). Also, U.S. Pat. No. 4,166,763 discloses an enzyme for use in analysis of lactic acid whereby the lactic acid is oxidized to produce pyruvate and hydrogen peroxide. The hydrogen peroxide is then measured colorometrically. These methods are all time consuming and expensive and fail to provide a means to rapidly detect lactic acid directly.

Clark has described a method for directly measuring lactic acid and lactate levels by means of a polarographic analysis in U.S. Pat. No. 4,467,811. However, Clark's invention requires that a sample of blood be taken and injected into a reaction chamber where the process takes place in vitro.

There is a genuine need in the art to provide an in vivo method which can continuously and instantaneously monitor lactic acid and lactate concentrations at specific sites in mammal bodies.

SUMMARY OF THE INVENTION

It is a primary object of the present invention to provide a method for monitoring lactic acid and lactate concentrations in vivo.

It is a further object of the present invention to provide a method for continuous monitoring of lactic acid and lactate concentrations in vivo.

Another object of the present invention is to provide a method for instantaneous monitoring of lactic acid and lactate concentrations in vivo.

Another object of the present invention is to provide a means for monitoring lactic acid and lactate concentrations which is of a small size particularly suited to incorporation on various catheters.

Still another object of the present invention is to provide a method for monitoring lactic acid and lactate concentrations in vivo which can be directed under fluoroscopic control to monitor the levels at specific sites within a mammal body.

In accordance with the foregoing objectives, the present invention provides a multi-layered membrane for incorporation on a catheter to allow for lactic acid and lactate concentration monitoring. This multi-layer membrane consists of an outer membrane of polycarbonate, a middle membrane of lactate oxidase enzyme immobilized in gluteraldehyde, and an inner membrane of high density cellulose acetate. The inner membrane is attached to the catheter with cyanoacrylate glue and the membrane completely covers the platinum anode. The tip of the cathether is a silver-silver chloride cathode. The catheter can be directed under fluoroscopic control to a precise location within a mammal body and hence, the lactic acid and lactate levers at a specific site within the body may be monitored.

Electrical connections are made between the cathode and anode with a potential source of a modified Yellow Springs Instruments Model 25 Oxidase Meter. This meter has ranges reading from 0–100 nanoamps, 0–200 nanoamps, 0–500 nanoamps, 0–1,000 nanoamps, and 0–1,500 nanoamps. It supplies a polarizing voltage of 700 mV and can be connected to a chart recorder to make hard copy records.

In vitro testing shows the device to have linear responses with lactate solutions ranging from 0 mL/L to 15 mM/L and stable current outputs ranging from 0–39 nanoamps. Linear responses are also obtained with whole blood, with lactate concentrations ranging from 0.8–2.2 mM/L. When the sensor equipped catheter was placed in the inferior vena cava of a heparinized, anesthetized dog infused intravaneously with a concentrated lactate solution, the sensor tracked the changes in blood lactic concentrations for more than an hour.

DESCRIPTION OF THE DRAWING

FIG. 4 is a composite plot of blood lactate concentrations and sensor output for each observation during intravenous infusion of a concentrated lactate solution in an anesthetized dog where the lactate sensor was located in the inferior vena cava.

DESCRIPTION OF THE PREFERRED EMBODIMENTS

Figure 1:
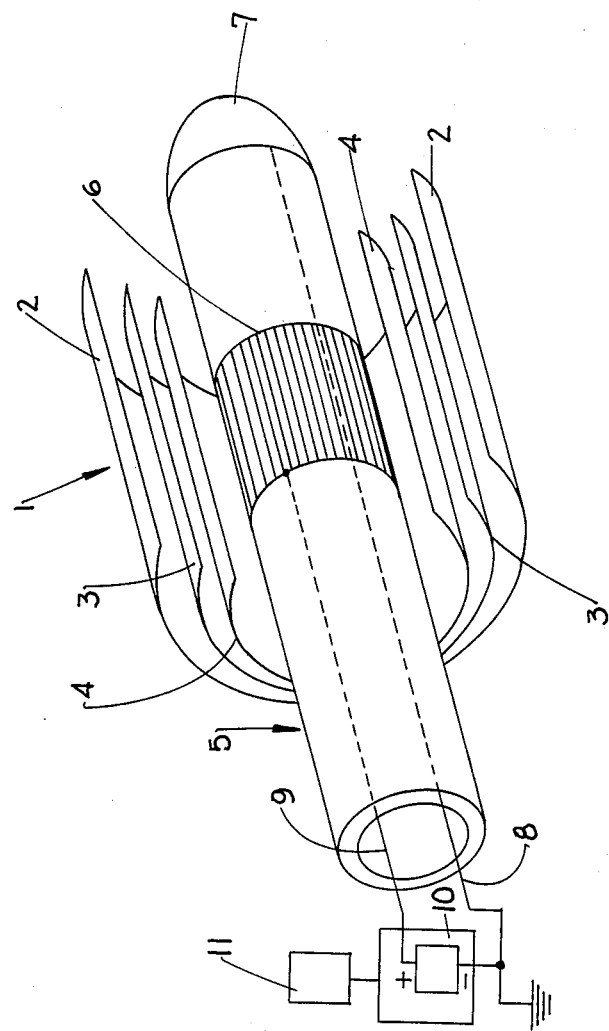
FIG. 1 is a diagrammatical illustration of a catheter equipped with the polarographic sensor of the present invention.

An apparatus in accordance with the present invention comprises a multi-layer membrane, generally designated 1, and shown in the exploded position in FIG. 1. This multi-layer membrane has been described in detail in U.S. Pat. No. 4,467,811 and can be purchased from Yellow Springs Instruments Co., Inc. An outer membrane 2 preferably is a 0.03 micron pore size perforated polycarbonate film having a thickness of 5 microns, nitrogen flow rate of 25 ml/min/cm$^2$ at 10 psi and having $6 \times 10^8$ holes/cm$^2$. An inner layer 4 preferably is a high density cellulose acetate membrane with a much smaller pore size than that of outer membrane 2, which excludes ascorbic acid and most other potentially interfering substances from passing inward while still allowing hydrogen peroxide, oxygen, water, and salts to pass through. This inner layer 4 measures 1 micron in thickness. A middle layer 3 is the oxidase enzyme layer wherein lactate oxidase is immobilized in gluteraldehyde, a cross-linking agent. In the case of lactate oxidase, a substantially catalase free oxidase is required. Such a highly purified lactate oxidase derived from Pediococcus Sp may be obtained from Fermco Biochemics, Inc. of Elk Grove Village, Ill., 60007. The enzyme layer 3 acts to bond layers 2 and 4 together, and is 1 micron thick, giving a total thickness of 7 microns for the multi-layer membrane. This membrane is attached to a catheter, generally designated 5, with cyanoacrylate glue, completely covering a platinum anode 6, which is set back from the outer tip of the catheter. This latter arrangement allows the membrane covered anode to be situated freely within the blood vessels without contacting the sides, thus allowing free circulation of blood around the surface of the membrane and the catheter, since the overall diameter of the catheter (including the membrane covering) is not greater than 2.0 mm, and preferably is not greater than about 1.5 mm.

The tip of the catheter 5 is cathode 7 consisting of a bead of silver-silver chloride which is 50% silver and 50% silver chloride by weight, obtained from In Vivo Metrics, Inc., Healdsburg, Calif. Electrical connection 8 is made between the cathode and a potential source, and electrical connection 9 is made between the anode and the potential source of a modified Yellow Springs Instruments Model 25 Oxidase Meter with ranges as noted previously, indicated schematically at 10 in FIG. 1. A strip chart recorder, indicated schematically at 11, may be connected to the meter 10.

The outer membrane 2 of polycarbonate material has a nominal pore size which allows the inward passage of small molecules such as lactic acid, lactate and oxygen. Once the lactate has entered the middle layer 3, it reacts with the lactate oxidase immobilized in this layer to form pyruvate and hydrogen peroxide. This is demonstrated by the following equation:

$$\text{L-lactate} + O_2 \xrightarrow{\text{L-Lactate Oxidase}} \text{Pyruvate} + H_2O_2.$$

The hydrogen peroxide produced by this reaction then diffuses through the inner membrane 4 to contact the platinum anode 6. The Model 25 potential source maintains the anode 6 at a potential of +0.7 volts with respect to the silver-silver chloride cathode 7. The reaction of the hydrogen peroxide occurring at the anode 6 yields a current linearly proportional to the concentration of lactate. This reaction is demonstrated by the following equation:

$$H_2O_2 \rightarrow 2H^+ + O_2 + 2e^-.$$

The circuit is then completed at the silver cathode 7 wherein the following reaction takes place:

$$2AgCl + 2e^- \rightarrow 2Ag + 2Cl^-.$$

Critical for the present invention is the use of a lactate oxidase which is substantially catalase free. Catalase is an enzyme which quickly binds and destroys hydrogen peroxide. Hence, there would be no hydrogen peroxide for the electrode to detect providing a lactate concentration measurement. Therefore, the substantially catalase free lactate oxidase derived from Pediococcus Sp and commercially available is recommended.

The hydrogen peroxide produced by reaction 2 passes through the inner membrane 4 and causes a current flow across the cell which is directly proportional to the quantity of hydrogen peroxide diffusing through the membrane 4. The determination of the current flowing across the cell by the oxidase meter is a function of the amount of hydrogen peroxide formed and is an indication of the amount of lactic acid or lactate in the sample. This measurement is a kinetic measurement and the production of hydrogen peroxide is directly proportional to the amount of lactate in the sample.

Figure 2:
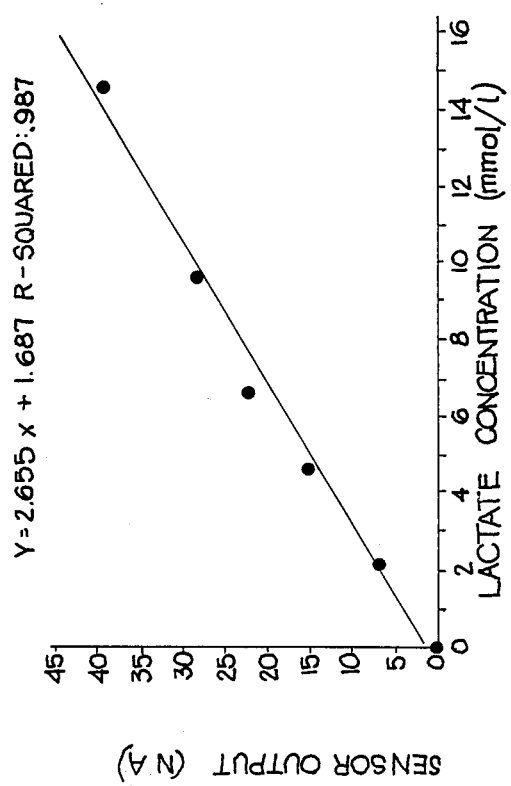
FIG. 2 is a plot of current versus lactate concentration for a crystalloid solution.
Figure 3:
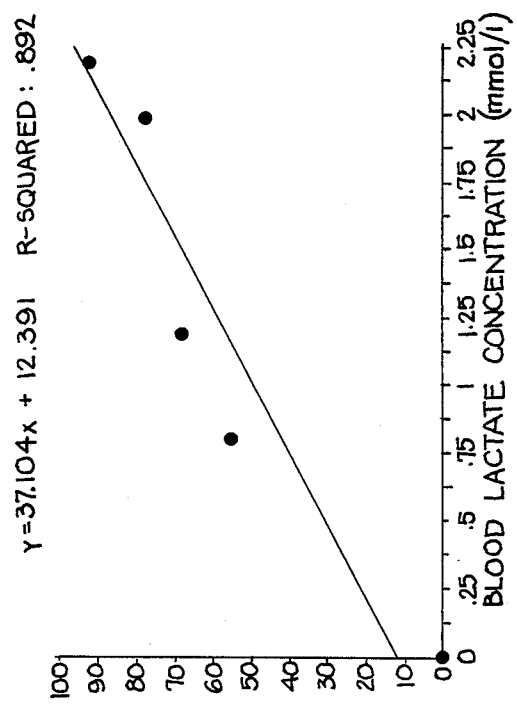
FIG. 3 is a plot of current versus lactate concentration for a whole blood sample.

By incorporating the membrane polarographic instrument on a catheter according to the present invention, continuous readings may be taken of lactate levels at specific sites in the human body, as illustrated by FIGS. 2-4. In an experiment with the heparinized, anesthetized dog, the sensor was placed in the inferior vena cava of its heart. The dog was then infused intravenously with a concentrated lactate solution and the sensor tracked the changes in blood lactate concentrations for more than one hour.

The present method provides a means to measure lactate, lactic acid, as well as lactic acid derivatives, including phenyl lactate and ethyl lactate, which react with lactic oxidase to produce hydrogen peroxide. Simply by substituting oxidase enzymes such as glucose oxidase or alcohol oxidase for the lactic oxidase enzyme, dextrose and alcohol may also be studied. The catheter tip sensor may be used within the vascular system and body cavities of mammals, including humans, as well as in vitro in biological, biochemical, and industrial applications.

I claim as my invention:

1. An apparatus for the in vivo or in vitro measurement of concentrations of lactate, lactic acid, and derivatives thereof in blood at a specific site in a mammal body, wherein said lactate, lactic acid, or derivative thereof is reacted with an oxidase enzyme to produce pyruvate and hydrogen peroxide and said hydrogen peroxide is measured polarographically, comprising:
   (a) a catheter;
   (b) an uncoated cathode positioned on and forming a tip of said catheter;
   (c) an anode positioned behind said cathode in spaced relation to said tip and surrounding said catheter wherein said anode and said cathode are electrically insulated from each other;
   (d) a multi-layered membrane completely surrounding said anode;

(e) a potential source providing an electrical connection between said anode and said cathode; and (f) an oxidase meter connected to said potential source and adapted to detect a current produced between said anode and said cathode when said hydrogen peroxide diffuses through said membrane to contact said anode.

2. The apparatus of claim 1 wherein said membrane comprises:

(a) an outer layer adapted to be in contact with said blood;

(b) an inner layer in contact with said anode; and (c) a middle layer connecting said outer and said inner layers.

3. The apparatus of claim 2 wherein said outer layer comprises perforated polycarbonate film.

4. The apparatus of claim 3 wherein said perforated polycarbonate film has a pore size of 0.03 microns, $6 \times 10^8$ holes per $cm^2$, and a nitrogen flow rate of 25 ml/min/$cm^2$ at the 10 psi.

5. The apparatus of claim 2 wherein said inner layer comprises high density cellulose acetate.

6. The apparatus of claim 5 wherein said inner layer has a small enough pore size to exclude ascorbic acid and most other potentially interfering substances while still allowing $H_2O_2$, $O_2$, $H_2O$, and salt to pass through.

7. The apparatus of claim 5 wherein said inner layer is attached to said anode with cyanoacrylate glue.

8. The apparatus of claim 2 wherein said middle layer comprises lactate oxidase immobilized in gluteraldehyde.

9. The apparatus of claim 8 wherein said middle layer bonds said outer and said inner layers together.

10. The apparatus of claim 2 wherein said outer layer is 5 microns thick, said middle layer is 1 micron thick and said inner layer is 1 micron thick.

11. The apparatus of claim 1 wherein the overall diameter of said membrane-covered cathether is not greater than 2.0 mm.

12. The apparatus of claim 1 wherein said cathode comprises a bead of silver-silver chloride.

13. The apparatus of claim 1 wherein said anode comprises a platinum ring.

14. A polarographic sensor for continuous monitoring of levels of lactic acid, lactate and derivatives thereof in blood at a specific site in a mammal body comprising:

(a) a catheter having an uncoated cathode positioned on and forming an outer tip thereof and an anode positioned behind said cathode in spaced relation to said tip and electrically insulated from said cathode;

(b) a potential source connecting said anode and said cathode;

(c) a membrane surrounding said anode wherein said membrane further comprises an inner layer and an outer layer spacially separated; and (d) an oxidase enzyme solution situated between said outer and said inner layers.

15. The polarographic sensor of claim 14 wherein said outer layer is adapted to be in contact with said blood and said inner layer is in contact with said anode.

16. The polarographic sensor of claim 15 wherein said inner layer is attached to said anode with cyanoacrylate glue.

17. The polarographic sensor of claim 14 wherein said outer layer comprises perforated polycarbonate film.

18. The polarographic sensor of claim 17 wherein said perforated polycarbonate film has a pore size of 0.03 microns, $6 \times 10^8$ holes per $cm^2$, and a nitrogen flow rate of 25 ml/min/$cm^2$ at the 10 psi.

19. The polarographic sensor of claim 14 wherein said inner layer comprises high density cellulose acetate.

20. The polarographic sensor of claim 18 wherein said inner layer has a small enough pore size to exclude ascorbic acid and most other potentially interfering substances while still allowing $H_2O_2$, $O_2$, $H_2O$, and salt to pass through.

21. The polarographic sensor of claim 14 wherein said outer layer is 5 microns thick, said inner layer is 1 micron thick, and said inner and said outer layer are spatially separated by a distance of 1 micron.

22. The polarographic sensor of claim 14 wherein the overall diameter of said membrane covered catheter is not greater than 2.0 mm.

23. A method for the continuous in vivo measurement of lactate, lactic acid, derivatives thereof, alcohol and dextrose at a specific site in a mammal body comprising:

(a) providing a catheter having an anode and a cathode, said cathode forming an outer tip of said catheter and said anode being positioned behind said cathode in spaced relation to said tip and electrically insulated from said cathode;

(b) said anode being surrounded with an inner membrane, a middle membrane, and an outer membrane, said membrane-covered anode having a diameter not greater than 2.0 mm;

(c) connecting said anode and said cathode with a potential source;

(d) connecting said anode to an oxidase meter;

(e) inserting said catheter into the vascular system of said mammal body in such manner as to permit free circulation of blood around said membranes and said catheter; and (f) directing said catheter to a specific site with fluoroscopy.

24. The method of claim 23 wherein said middle membrane comprises an oxidase enzyme solution immobilized in gluteraldehyde.

* * * * *